US006830920B2

(12) United States Patent
Davidson et al.

(10) Patent No.: US 6,830,920 B2
(45) Date of Patent: Dec. 14, 2004

(54) RAPID GENERATION OF RECOMBINANT ADENOVIRAL VECTORS

(75) Inventors: Beverly L. Davidson, Iowa City, IA (US); Richard Anderson, Coralville, IA (US); Ronald Haskell, West Liberty, IA (US); Haibin Xia, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/521,524

(22) Filed: Mar. 8, 2000

(65) Prior Publication Data

US 2002/0098571 A1 Jul. 25, 2002

(51) Int. Cl.$^7$ ............... C12N 15/64; C12N 7/00; C12N 5/00; C12N 15/00; C12N 15/86; C12N 15/861; C07H 21/04

(52) U.S. Cl. ............... 435/235.1; 435/91.42; 435/320.1; 435/325; 435/462; 435/463; 435/466; 435/475; 435/476; 435/477; 536/23.72

(58) Field of Search ............... 435/462, 463, 435/466, 91.42, 235.1, 320.1, 325, 475, 477, 5, 69.3, 70.1, 457, 472, 237; 536/23.72

(56) References Cited

U.S. PATENT DOCUMENTS

| | | | | |
|---|---|---|---|---|
| 5,747,072 A | * | 5/1998 | Davidson et al. | 424/93.2 |
| 5,922,576 A | * | 7/1999 | He et al. | 435/91.41 |
| 5,965,441 A | * | 10/1999 | Breakefield et al. | 435/456 |
| 6,251,677 B1 | * | 6/2001 | Wilson et al. | 435/457 |
| 6,251,957 B1 | * | 6/2001 | Wilson et al. | 424/85.2 |

FOREIGN PATENT DOCUMENTS

| | | | | |
|---|---|---|---|---|
| EP | 0955373 | | 11/1999 | ........... C12N/15/86 |
| WO | WO-98/32860 | | 7/1998 | ........... C12N/15/33 |
| WO | WO 98/39035 | * | 11/1998 | |

OTHER PUBLICATIONS

Aoki et al. 1999. Efficient generation of recombinant adenoviral vectors by Cre–lox recombination in vitro. Molecular Medicine. vol. 5, pp. 224–231.*

Krougliak et al. 1995. Development of cell lines capable of complementing E1, E4, and protein IX defective adenovirus type 5 mutants. vol. 6, pp. 1575–1586.*

Chartier et al., 1996. Efficient generation of recombinant adenovirus vectors by homologous recombination in *Escherichia coli*. Journal of Virology. vol. 70, No. 7, pp. 4805–4810.*

Aoki et al. Molecular Medicine. 1999; 5: 224–231.*

Chinnadurai et al. Journal of Virology. 1979; 32 (2): 623–628.*

Krougliak et al. Human Gene Therapy. 1995; 6: 1575–1586.*

Chartier et al. Journal of Virology. 1996; 70 (7): 4805–4810.*

Stratford–Perricaudet et al. (Journal of Clinical Investigation. 1992; 90: 626–630).*

Anderson, R.D., "A simple method for the rapid generation of recombinant adenovirus vectors", *Gene Therapy*, 7, (2000), pp. 1034–1038.

Danthinne, X., et al., "Production of first generation adenovirus vectors: a review", *Gene Therapy, vol. 7* (2000), pp. 1707–1714.

He, T–C., et al., "A simplified system for generating recombinant adenoviruses", *PNAS USA, vol. 95* (1998), pp. 2509–2514.

(List continued on next page.)

Primary Examiner—Shanon Foley
(74) Attorney, Agent, or Firm—Fish & Richardson P.C., P.A.

(57) ABSTRACT

The invention provides a novel Adenovirus backbone plasmid, which when co-transfected with a shuttle vector, allows for production of recombinant viruses quickly and easily. The present invention also provides host cells and a cloning system for generating recombinant adenoviruses.

18 Claims, 3 Drawing Sheets-

OTHER PUBLICATIONS

Bartlett, J.S., et al., "Genetics and Biology of Adeno–Associated Virus", *Chapter 4: Viral Vectors ——Gene Therapy and Neuroscience Applications*, Edited by M.G. Kaplitt, MD, PhD:Academic Press,(1995), pp. 55–73.

Bett, A.J., et al., "An efficient and flexible system for construction of adenovirus vectors with insertions or deletions in early regions 1 and 3", *PNAS USA, 91*, (Sep. 1994), pp. 8802–8806.

Crouzet, J., et al., "Recombinational construction in *Escherichia coli* of infectious adenoviral genomes", *PNAS USA, 94*, (Feb. 1997), pp. 1414–1419.

Davidson, B.L., et al., "Adenoviral–Mediated Gene Transfer: Potential Therapeutic Applications", *Chapter 11:Viral Vectors ——Gene Therapy Neuroscience Applications*, Edited by M.G. Kaplitt, MD, PhD: Academic Press, (1995), pp. 173–192.

Davidson, B.L., et al., "Expression of *Escherichia coli* β–Galactosidase and Rat HPRT in the CNS of Macaca mulatta Following Adenoviral Mediated Gene Transfer", *Experimental Neurology, 125*, (1994), pp. 258–267.

Davis, A.V., et al., "High throughput method for creating and screening recombinant adenoviruses", *Gene Therapy, 5*, (1998), pp. 1148–1152.

Fallaux, F.J., et al., "Characterization of 911: A New Helper Cell Line for the Titration and Propagation of early region 1–Deleted Adenoviral Vectors", *Human Gene Therapy, 7*, (Jan. 1996), pp. 215–222.

Fallaux, F.J., et al., "New Helper Cells and Matched Early region 1–Deleted Adenovirus Vectors Prevent Generation of Replication–Competent Adenoviruses", *Human Gene Therapy, 9*,pp. 1909–1917.

Fu, S., et al., "Use of the Cosmid Adenoviral Vector Cloning System for the In Vitro Construction of Recombinant Adenoviral Vectors", *Human Gene Therapy, 8*, (Jul. 1997), pp. 1321–1330.

Graham, F.L., et al., "Characteristics of a Human Cell Line Transformed by DNA from Human Adenovirus Type 5", *J. Gen. Virol., 36*, (1977), pp. 59–72.

Hardy, S., et al., "Construction of Adenovirus Vectors Through Cre–lox Recombination", *Journal of Virology, 71 (3)*, (Mar. 1997), pp. 1842–1849.

Imler, J–L., et al., "Novel complementation cell lines derived from human lung carcinoma A549 cells support the growth of E1–deleted adenovirus vectors",.

*Gene Therapy, 3*, (1996), pp. 75–84.

Jones, N., et al., "Isolation of Deletion and Substitution Mutants of Adenovirus Type 5", *Cell, 13*, (Jan. 1978), pp. 181–188.

Ketner, G., et al., "Efficient manipulation of the human adenovirus genome as an infectious yeast artificial chromosome clone", *PNAS USA, 91*, (Jun. 1994), pp. 6186–6190.

Kojima, H., et al., "Generation of Recombinant Adenovirus Vector with Infectious Adenoviral Genome Released from Cosmid–Based Vector by Simple Procedure Allowing Complex Manipulation", *Biochemical and Biophysical Research Communications, 246*, (1998), pp. 868–872.

Lochmüller, H., et al., "Emergence of Early Region 1–Containing Replication–Competent Adenovirus in Stocks of Replication–Defective Adenovirus Recombinants (ΔE1 + ΔE3) During Multiple Passages in 293 Cells", *Human Gene Therapy, t*, (Dec. 1994), pp. 1485–1491.

Mizuguchi, H., et al., "Efficient Construction of a Recombinant Adenovirus Vector by an Improved In Vitro Ligation Method", *Human Gene Therapy, 9*, (Nov. 1998), pp. 2577–2583.

NG, P., et al., "A High–Efficiency Cre/loxP–Based System for Construction of Adenoviral Vectors", *Human Gene Therapy, 10*, (Nov. 1999), pp. 2667–2672.

Samulski, R.J., et al., "Helper–Free Stocks of Recombinant Adeno–Associated Viruses: Normal Integration Does Not Require Viral Gene Expression", *Journal of Virology, 63 (9)*, (Sep. 1989), pp. 3822–3828.

Schiedner, G., et al., "Genomic DNA transfer with a high-–capacity adenovirus vector results in improved in vivo gene expression and decreased toxicity", *Nature Genetics, 18*, (Feb. 1998), pp. 180–183.

Shenk, T., "Group C Adenoviruses as Vectors for Gene Therapy", *Chapter 3: Viral Vectors ——Gene Therapy and Neuroscience Applications*, Edited by M.G. Kaplitt, MD, PhD:Academic Press, (1995), pp. 43–54.

Souza, D.W., et al., "Novel Cloning Method for Recombinant Adenovirus Construction in *Escherichia coli*", *BioTechniques, 26 (3)*, (Mar. 1999), pp. 502–508.

Wohlgemuth, J.G., et al., "Long–trem gene expression from autonomously replicating vectors in mammalian cells", *Gene Therapy, 3*, (1996), pp. 503–512.

* cited by examiner

SEQUENCE LISTING

<160> NUMBER OF SEQ ID NOS: 3

<210> SEQ ID NO 1
<211> LENGTH: 20
<212> TYPE: DNA
<213> ORGANISM: Human adenovirus type 5

<400> SEQUENCE: 1
ccagtgacga cgaggatgaa                                                   20

<210> SEQ ID NO 2
<211> LENGTH: 22
<212> TYPE: DNA
<213> ORGANISM: Human adenovirus type 5

<400> SEQUENCE: 2
ccgtattcct ccggtgataa tg                                                22

```
-continued

<210> SEQ ID NO 3
<211> LENGTH: 21
<212> TYPE: DNA
<213> ORGANISM: Human adenovirus type 5

<400> SEQUENCE: 3
acaagacctg caaccgtgcc c                                              21
```

RAPID GENERATION OF RECOMBINANT ADENOVIRAL VECTORS

Portions of the present invention were made with support of the United States Government via a grant from the National Institutes of under grant number HD33531 and DK54759. The U.S. Government therefore may have certain rights in the invention.

BACKGROUND OF THE INVENTION

Adenoviruses (Ad) are double-stranded linear DNA viruses with a 36 kb genome. Several features of adenovirus have made them useful as a transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Adenovirus vectors also are very important tools for deciphering the role of various proteins in biological processes in vitro and in vivo[1-4]. They are commonly used because they infect a wide variety of cell types, provide very high protein expression, and when purified show little prep-to-prep variation. The technology to generate the viruses requires only basic laboratory techniques. However, to progress from a cDNA of interest in a shuttle vector to a purified, wildtype-free virus traditionally involves many steps and requires a significant time investment.

Several approaches traditionally have been used to generate the recombinant adenoviruses. One approach involves direct ligation of restriction endonuclease fragments containing a transgene to portions of the adenoviral genome. The low efficiency of large fragment ligations and the scarcity of unique restriction sites, however, have made this approach technically challenging.

Alternatively, the transgene may be inserted into a defective adenovirus by homologous recombination results. The desired recombinants are identified by screening individual plaques generated in a lawn of complementation cells. Though this approach has proven useful, the low efficiency of homologous recombination, the need for repeated rounds of plaque purification, and the long times required for completion of the viral production process has hampered more widespread use of adenoviral vector technology.

Most adenovirus vectors are based on the adenovirus type 5 (Ad5) backbone in which an expression cassette containing the foreign gene has been introduced in place of the early region 1 (E1) or early region 3 (E3). Viruses in which E1 has been deleted are defective for replication and are propagated in human complementation cells (e.g., 293 or 911 cells), which supply the missing gene products provide the E1 and pIX products in trans.

Many laboratories continue to use standard methods of homologous recombination with shuttle plasmids and full-length Ad backbones (restricted in E1) for generation of vectors for basic research[5]. However, the time required to generate the vectors can range from a best-case scenario of 2 months to many months. Also, there may be wildtype contamination in the initial plaque isolation that necessitates further, time intensive, serial plaque isolations and amplification. Recent efforts have been directed at solving both the time and wildtype contamination problems. These include E. coli recombination methods[6], ligation of cDNA directly into plasmids containing E1 deleted full-length viral DNA[7-9], and an in vitro enzymatic recombination using Cre-loxP shuttles and backbone viral DNA[10-12].

The advantages of these systems are that the repetitive plaque isolation to purify the viral particle can be avoided because there is no[6,8,12] or limited[10] wildtype viral DNA input. Thus, there is a reduction in the amount of time it takes to progress from the transfection of viral DNA to amplified, purified virus. However, these methods also have their drawbacks. For the E. coli recombination using plasmids containing adenovirus genomes, the system has high fidelity, but is inefficient and requires the screening of many bacterial colonies. This results in a significant time commitment even before transfection of recombinant DNA into E1-expressing cells such as HEK293 cells[13]. Similarly, ligation and recombinase methods require that several steps be completed before transfection into helper cell lines to generate virus. These recently developed methods are useful for making one or two viruses, but they are cumbersome if studies require multiple viruses to be generated.

Thus, to progress from a cDNA of interest in a shuttle vector to a purified, wild-type free virus is cumbersome as it involves many steps and can require a significant time investment. The time required to generate the vectors can range from a best-case scenario of two months to many months. Also, there may be wild-type contamination in the initial plaque isolation that necessitates further, time intensive, repetitions of plaque isolation and amplification.

Therefore, there is a continuing need for improved methods to accomplish multiple vector production in a simple and time-efficient manner.

SUMMARY OF THE INVENTION

The invention provides an Adenovirus (Ad) backbone plasmid comprising an Ad genome lacking map units 0 to 9.2, starting with a lefthand ITR. Further, any or all open reading frames constituting E4 or E3 may be modified in the Ad backbone plasmid. The modification may be a substitution, insertion, or deletion of one or more nucleotides, including being modified to contain a multiple cloning site. The Ad backbone plasmid may contain one or more genes required for Herpes Simplex Virus (HSV) packaging and/or an HSV origin of replication within the E3 region or other locations within the backbone. The plasmid may further comprise HSV Amplicon sequences required for packaging and replication, and the Amplicon sequences may be positioned on either side of the Ad left and right ITRs.

The invention further provides a shuttle plasmid comprising Ad sequences from 0 to 1 and 9.2 to 16.1 map units of an Ad genome. PacI restriction endonuclease sites may flank either end of the Ad sequences, and a multiple cloning site may be positioned between 1 and 9.2 map units. The shuttle plasmid may contain a sequence encoding a gene of interest, and may contain a novel promoter, inducible promoter or other sequence used to drive expression from a transgene.

The present invention also provides a cloning system for generating recombinant adenovirus comprising any of the Ad backbone plasmids described above and any of the shuttle plasmids described above.

The present invention further provides a host cell comprising any of the Ad backbone plasmids described above and any of the shuttle plasmids described above. The cell may express E1 sequences and pIX necessary for supporting adenovirus replication, and may express E4 sequences required for amplification of viruses generated with the modified Ad backbone. The cell may be an animal cell.

The present invention also provides method for rapidly producing recombinant adenovirus comprising contacting a host cell with any of the Ad backbone plasmids described above and any of the shuttle plasmids described above. This method may include the additional step of serially amplifying virus produced by the host cell and a step of detecting the presence of wild type virus. The shuttle plasmid used in the method may comprise a sequence encoding a gene of interest.

BRIEF DESCRIPTION OF THE DRAWINGS

FIG. 1. Generation of plasmids required for the RAPAd.I™ system. To make the pacAd5 9.2–100, pacAd5RSVK-NpA was first digested with NheI/XbaI and religated to produce pacAd5 9.2–16.1. PacAd 9.2–16.1 was digested with ScaI, and co-transfected into E. coli BJ5183 cells along with ClaI restricted pTGRSVhGFP. The BJ5183 E. coli support efficient homologous recombination[6], and facilitated the generation of pacAd5 9.2–100. PacAd5 9.2–100 DNA was further amplified in E. coli DH5α and purified. The backbone is devoid of adenovirus sequences from 0 to 9.2 m.u. Plasmid sequences were confirmed with the assistance of the University of Iowa DNA sequencing facility.

FIG. 2. Generation of recombinant adenovirus using the RAPAd.I™ system. A. The shuttle plasmid pacAd5RSVEGFP was constructed by cloning the XhoI/NotI fragment from pEGFP-N1 (Clonetech, Palo Alto, Calif.) into the XhoI and NotI restriction sites of the pacAd5RSVK-NpA shuttle vector (FIG. 1). PacAd5RSVEGFP and pacAd5 9.2–100 (15 and 4 μg, respectively) were digested independently with PacI (New England Biolabs, Beverly, Mass.) and precipitated in transfection buffer (20 mM HEPES, 136 mM NaCl, 5 mM KCl, 0.7 mM $Na_2HPO_4$, 5.5 mM glucose, pH 7.1, and a final concentration of 125 mM $CaCl_2$). The precipitate was added to 60 mm plates containing 50% confluent HEK293 cells and fresh DMEM containing 2% fetal bovine serum, 100 U/mL penicillin and 100 μg/mL streptomycin (Mediatech Cellgro, Va.). Homologous recombination in HEK293 cells lead to generation of RAPAd5.RSVEGFP. B. EGFP expression detected after co-transfection of pacAd5RSVEGFP and pacAd5 9.2–100. Plates were examined from 1 to 8 days for the presence of viral foci by fluorescence microscopy using an inverted fluorescence microscope (Olympus IX70, Melville, N.Y.). As shown in the representative photomicrographs, RAPAd5.RSVEGFP foci produce a comet-like appearance at approximately 6 days. (Magnification=10×).

DETAILED DESCRIPTION OF THE INVENTION

Recombinant adenoviruses are useful vectors for basic research. When used in delineating protein function, vectors that contain a given transgene with mutations or alterations to the coding sequence are compared at the same time. Methods to generate multiple vectors simultaneously in a short period of time, however, are cumbersome.

Adenoviruses can be made by standard transfection of a shuttle plasmid and viral DNA backbone into HEK 293 cells. Homologous recombination occurs in vivo, and recombinant virus can be isolated and propagated. The major drawback of this technique is that the starting viral DNA backbone, restricted of E1 containing sequences, must be 100% free of full-length Ad DNA. Otherwise, varying amounts of wild-type virus are also propagated.

The present invention is a streamlined method of producing adenovirus vectors that is both simpler and quicker than previous methods. Previous work by the inventors and others indicate that vector preparations are typically contaminated with varying amounts of wildtype virus when standard methods of homologous recombination between adenovirus backbones (digested to remove the packaging signal and E1-containing sequences) and shuttle plasmids are used. The wildtype is probably a result of the input adenovirus-DNA backbone being incompletely digested. In most cases the level of wildtype contamination is unacceptably high, and the desired recombinant virus must be further isolated through repetitive, time-consuming plaque purification. An adenoviral genome devoid of sequences necessary for packaging and replication would greatly reduce or eliminate production of wildtype virus, eliminating the need for plaque purification. A novel Ad backbone was generated devoid of the left-hand ITR, the packaging signal, and E1 sequences. The novel backbone and shuttle plasmids constitute the RAPAd.I™ system.

Figure 1:
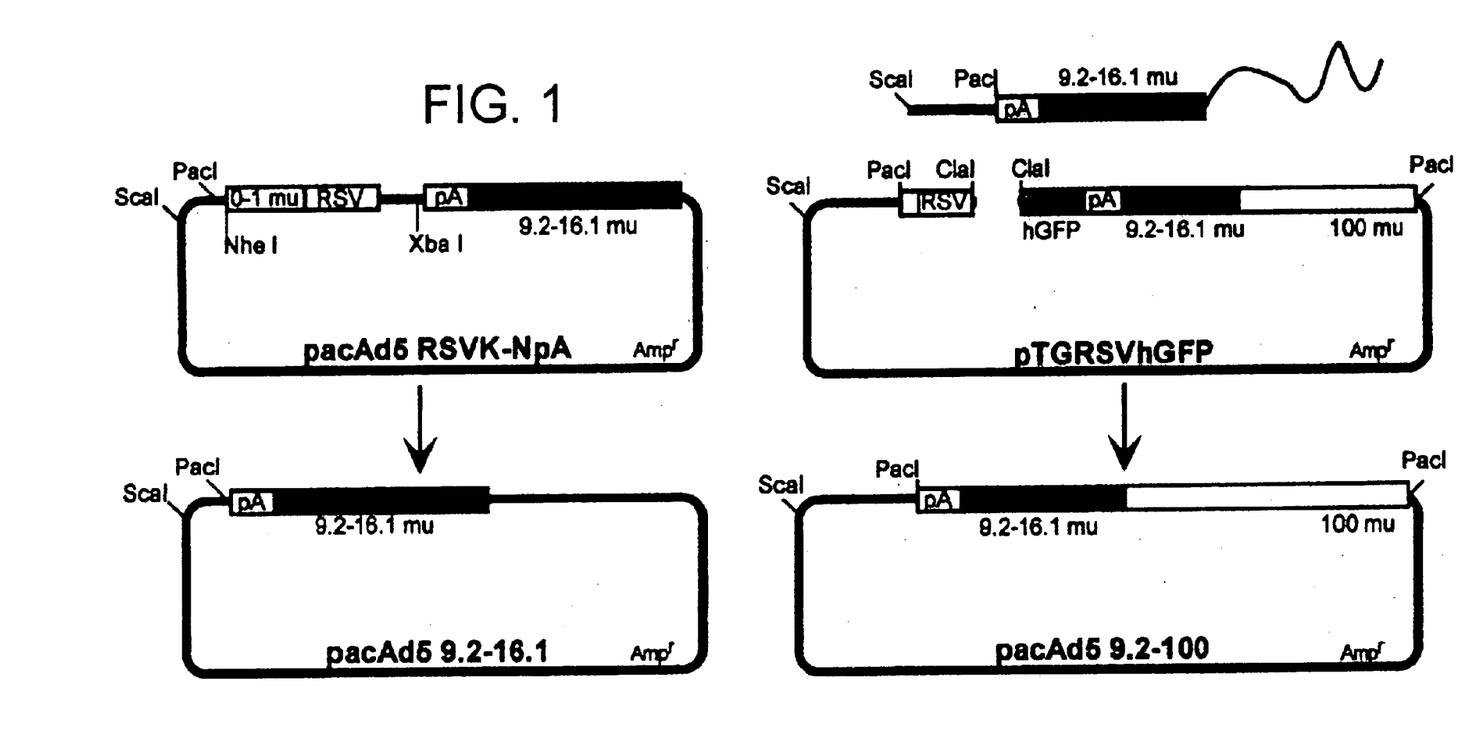

FIG. 1 illustrates an exemplary starting plasmid and the generation of an Ad backbone plasmid. The shuttle plasmid serves the standard purpose of 'shuttling' cDNAs of interest from a plasmid vector to a viral construct. In this case, the shuttle plasmid was also used to generate the backbone plasmid. An important aspect of the backbone plasmid pacAd5 9.2–100 is that 0 to 9.2 map units of the genome have been deleted, starting with the left-hand ITR. PacAd5 9.2–100 retains the 9.2–16.1 kb region homologous with sequences within existing shuttle vectors.

The RAPAd.I™ system allowed for generation of a reporter virus within two weeks, and the virus produced contained virtually no contaminating E1a sequences or replication competent virus. This compares favorably to current methods that take much longer[5,15-20]. The RAPAd.I™ system uses two components, a standard shuttle plasmid and the RAPAd.I™ backbone. The method is straightforward and requires very limited 'hands on' time from shuttle/backbone co-transfection to the isolation of virus particles. The RAPAd5.RSVGFP particles produced had roughly equivalent infectious titers as the standard viral genome/shuttle plasmid recombination method used frequently in many laboratories. The present virus particle isolation methods yield approximately 10 mL of $1 \times 10^{12}$ particles/mL. Thus, approximately 160 mL of wildtype-free virus particles (approximately $2 \times 10^{14}$ total particles) are produced by the fifteenth serial amplification, an amount likely to be more than adequate for most in vitro and in vivo gene transfer studies.

As stated, wildtype Ad genomes may arise from contaminating input viral genomes, or from recombination of overlapping Ad sequences found in HEK293 cell genomes. Cells harboring adenovirus E1 with limited surrounding Ad sequences have been made to decrease this latter possibility[21-23]. However, the present serial amplification results suggest that reversion to replication competent virus occur very rarely, if at all, in HEK293 cells. This is important since most investigators do not have access to alternative cell lines, or cannot justify the cost of their use. Thus, for most transgenes placed into adenovirus vectors, standard HEK293 cells can be used. However, when making recombinant viruses that express pro-apoptotic transgenes, a fragmented cellular genome may increase the potential for homologous recombination between overlapping adenovirus sequences within the genome and recombinant virus sequences. For such transgenes, anti-apoptotic agents or the use of cell lines containing E1 sequences may only be required to avoid generation of wildtype virus.

The RAPAd.I™ method is not limited to E1 a-deleted viruses, since alternative backbones can easily be moved into this system. For example, modifications to E3 and E4 could be made to the pacAd5 9.2–100 backbone. Deletions in E3 or E4 would provide additional space for larger expression cassettes, or could be used to insert a separate expression cassette, or as other non-essential genes are identified, they could be removed to allow for additional transgenes or for larger transgenes. Moreover, the novel backbone described could provide appropriate helper functions to allow for generation of adenovirus vectors fully devoid of adenovirus sequences except the ITRs and packaging signal ('gutless' vectors[24]) or adeno-associated virus vectors[25,26]. Similar to the recombinant adenovirus preparations reported herein, 'gutless' or adeno-associated virus vectors prepared with pacAd5.2-100 as helper has no contaminating wildtype adenovirus genomes.

The present novel backbone plasmid, when co-transfected with routinely used shuttle vectors into HEK 293 cells, allowed for production of recombinant viruses in an average of 14 days. The recombinant viruses had no detectable wildtype virus contamination by A549 plaque assay and only 3 to 300 E1a copies per $10^9$ adenovirus genomes by a sensitive PCR-based assay. Further culturing or serial amplification did not result in wildtype revertants nor did cultures show increased levels of E1 a copy number by quantitative PCR. Thus, recombinant adenovirus vectors can be produced very simply, rapidly and with little to no contaminating wildtype particles. This system facilitates the generation of multiple genetic variants by eliminating the need for time-consuming plaque purification, and the need to manipulate and screen very large plasmids.

Examples of various RAPAd™ backbone plasmids include the following.

RAPAd.I pacAd5 9.2–100 contains PacI-NotI site SV40pA signal SalI-SacII and Ad5 sequence starting at base pair 3328 (9.24 m.u.). This removes the left ITR packaging signal, E1A 26K and 32K, E1B 15K, 19K and 57K. The remaining adenovirus sequence is based on dl309 sequence.

RAPAd.III pacAd5 9.2–100/SwaI contains PacI-NotI site SV40pA signal SalI-SacII and Ad5 sequence starting at base pair 3328 (9.24 m.u.). A unique SwaI restriction site has replaced the NdeI site located in the fiber gene.

RAPAd.III pacAd5 9.2–100/E3Δ 1.8 contains PacI-NotI site SV40pA signal SalI-SacII and Ad5 sequence starting at base pair 3328 (9.24 m.u.). The Ad5 sequence is Ad5 wildtype sequence except for the removal of sequences between XbaI sites located at base pairs 28592 to 30470 (79.4 to 84.6 m.u.).

RAPAd.III pacAd5 9.2–100/E3Δ 2.6 contains PacI-NotI site SV40pA signal SalI-SacII and Ad5 sequence starting at base pair 3328 (9.24 m.u.). The Ad5 sequence is Ad5 wildtype sequence except for the removal of sequences between BglII sites located at base pairs 28132 to 30819 (78.1 to 85.6 m.u.).

RAPAd.III pacAd5 9.2–100/E3Δ 3.1 contains PacI-NotI site SV40pA signal SalI-SacII and Ad5 sequence starting at base pair 3328 (9.24 m.u.). The Ad5 sequence is Ad5 wildtype sequence except for the removal of sequences between 27865 to 30995 (77.4 to 86.09 m.u.).

RAPAd.III pacAd5 9.2–100/E3Δ-RSVntlacZ is the same as pacAd5 9.2–100/E3Δ except the RSV promoter and nt lacZ gene pA has replaced the Ad5 sequences between the XbaI sites. The RSVntlacZpA cassette reads from the left to the right as cloned into the RAPAd backbone. This cassette is cloned in the opposite direction.

RAPAd.III pacAd5 9.2–100/E3Δ-RSVEGFP is the same as pacAd5 9.2–100/E3Δ except the RSV promoter and EGFP gene pA has replaced the Ad5 sequences between the XbaI sites. The RSVEGFPpA cassette reads from the left to the right as cloned into the RAPAd backbone. This cassette is cloned in the opposite direction.

RAPAd.IV pacAd5 9.2–100/E4Δ contains PacI-NotI site SV40pA signal SalI-SacII and Ad5 sequence starting at base pair 3328 (9.24 m.u.). The Ad5 sequence is Ad5 wildtype sequence except for the removal of sequences between SmaI sites located at base pairs 33093 to 35460 (91.9 to 98.5 m.u.)

RAPAd.III/IV pacAd5 9.2–100/E3ΔE4orf6 contains PacI-NotI site SV40pA signal SalI-SacII and Ad5 sequence starting at base pair 3328 (9.24 m.u.). The Ad5 sequence is Ad5 wildtype sequence except for the removal of E4 sequences between SmaI sites located at base pairs 33093 to 35460 (91.9 to 98.5 m.u.). Also E3 is deleted between 28132 to 30819 (78.1 to 85.6 m.u.). There is also a unique PmeI site located at the junction which has the E4 orf6 cloned into it.

RAPAd. Δ Any or all remaining genes may be removed to allow for the production of 'gutless' adenovirus particles.

RAPAd.IV and RAPAd Δ require host cells expressing E1 sequences and E4 sequences required for amplification of viruses generated with the Ad backbone.

Examples of various RAPAd™ shuttles include the following.

A. RAPAd.I Shuttles pacAd5K-NpA contains PacI-NheI sites, 0–1 m.u. (base pair 1 to base pair 354 of Ad5) and the following unique restriction sites: KpnI, PmeI, XhoI, ClaI, HindIII, EcoRV, EcoRI, BamHI, SpeI, XbaI and NotI. It also contains an Sv40pA signal SalI-SacII and Ad5 sequence starting at base pair 3328 (9.24 m.u. to 16.1 m.u.).

pacAd5RSVK-NpA is the same as pacAd5K-NpA with the exception of the RSV promoter is between the 354 Ad5 base pair and the KpnI restriction site.

pacAd5CMVK-NpA is the same as above with the exception of the CMV promoter between the 354 base pairs and the KpnI site.

pacAd5 ires pA can be used for the expression of two genes of interest from a single promoter.

B. RAPAd.III Shuttles sfuAd5E3Δ 1.8 This plasmid is a key component of the RAPAd.III system. It contains the Ad5 sequences from 27331 to 28592 and 30470 to 32806 separated by single XbaI site. The entire Ad5 sequence is flanked by SfuI restriction sites used to release a fragment used to generate E3 deleted backbone plasmids via E. coli recombination.

sfuAd5E3Δ 2.6 E3 sequences have been removed from BglII sites located at base pairs 28132 to 30819 (78.1 to 85.6 m.u.). The entire Ad5 sequence is flanked by SfuI restriction sites used to release a fragment used to generate E3 deleted backbone plasmids via E. coli recombination.

sfuAd5E3Δ 3.1 Ad5 sequence is Ad5 wildtype sequence except for the removal of sequences between 27865 to 30995 (77.4 to 86.09 m.u.). The entire Ad5 sequence is flanked by SfuI restriction sites used to release a fragment used to generate E3 deleted backbone plasmids via E. coli recombination.

sfuAd5E3RSVK-NpA contains the Ad5 sequences from 27331 to 28592 and 30470 to 32806. The RSVK-NpA cassette from the RAPAd.I shuttle has been cloned into the region. There are 6 unique restriction sites available for subcloning a gene of interest: PmeI, ClaI, EcoRV, SmaI, SpeI and XbaI. These fragments are flanked by SfuI restriction site used to release a fragment to generate E3 modified backbone plasmids. This plasmid contains the cassette in the opposite direction also.

sfuAd5E3CMVmcspA is the same as above except it contains the CMV promoter and contains four unique restriction sites: EcoRI, ClaI, EcoRV and XhoI. This plasmid contains the cassette in the opposite direction also.

C. RAPAd.IV Shuttles pAd5E4Δ Ad5 sequences from 29509 to 33093 and 35460 to 35935. SmaI fragment removed which deletes the E4 coding region. Any or all of the cassettes used for the E3 shuttle can be placed in this region.

Elements of the present disclosure are exemplified in detail through the use of backbone plasmids and shuttles. However in light of this disclosure, numerous other possible backbone plasmids and shuttles will be apparent to those of skill in the art in addition to these set forth herein. Therefore, it will be understood that the following discussion is exemplary rather than exhaustive. In light of the techniques disclosed herein and the general recombinant techniques that are known in the art, the present invention renders possible the modification of the backbone plasmids or shuttle vectors to produce effective cloning systems in accordance with the present invention.

EXAMPLES

Example 1

Construction of an Expression Vector

Figure 2A:
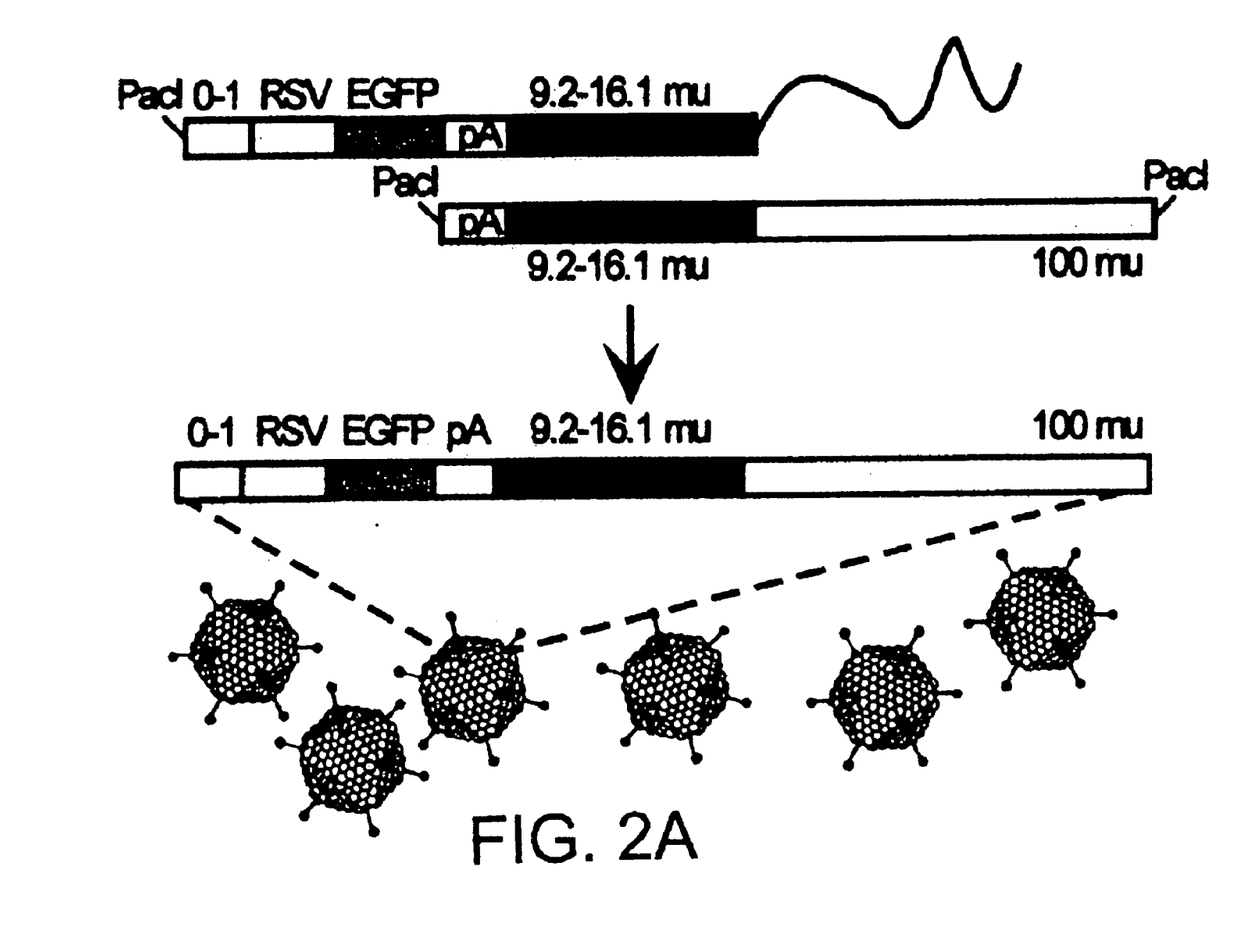
Figure 2B:
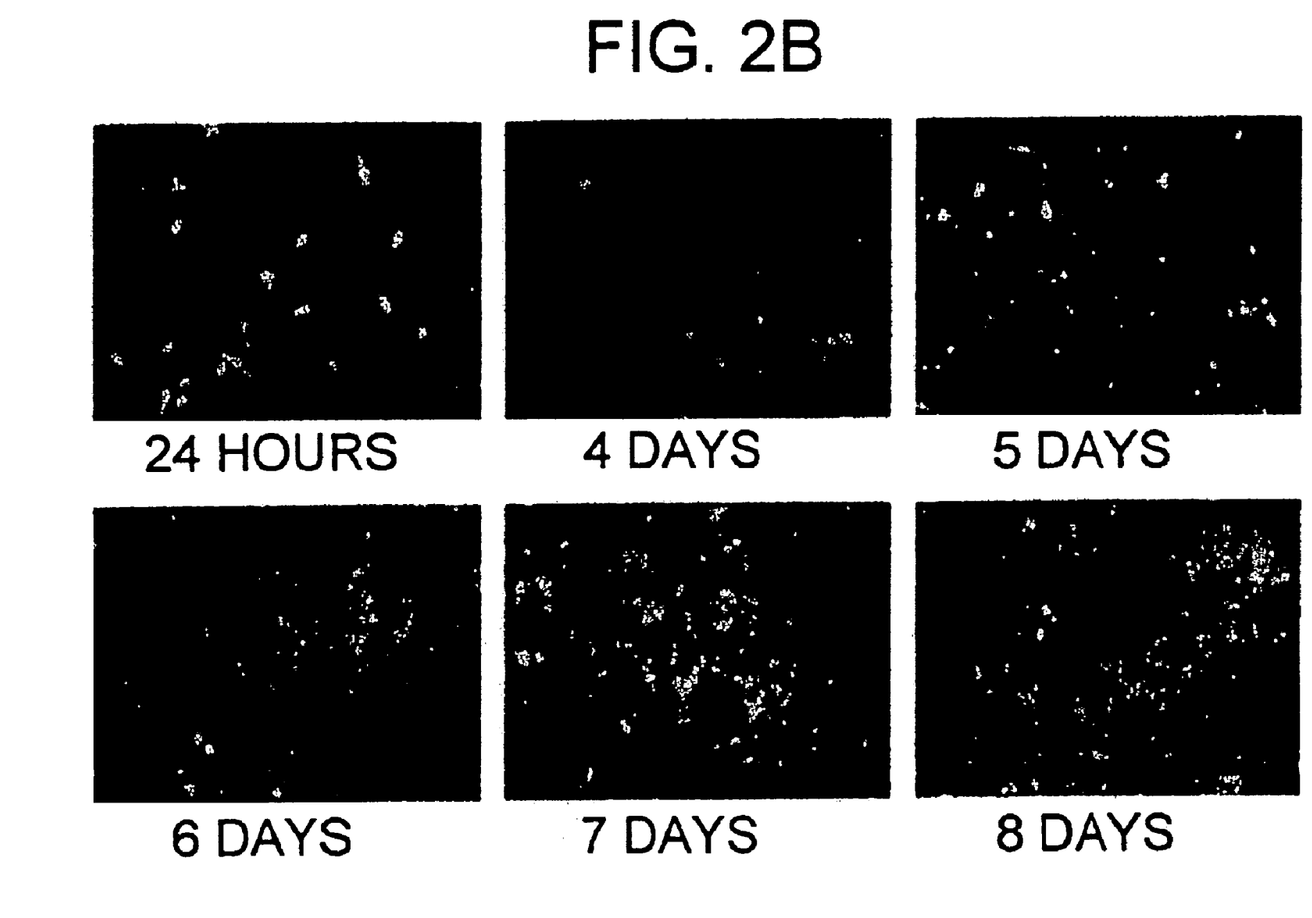

To test the RAPAd.I™ system, an eGFP-expressing virus was constructed. The shuttle plasmid pacAd5RSVEGFP and pacAd5 9.2–100 were digested with PacI and the mixture subsequently transfected into HEK293 cells using standard calcium phosphate methods as depicted in FIG. 2. As a control, HEK293 cells were transfected with pacAd5 9.2–100 alone. Viral foci were noted beginning day 6 in only the pacAdRSVEGFP/pacAd5 9.2–100 co-transfection (FIG. 2), with more foci evident over the next several days. The cells were harvested eight days after transfection, pelleted by low-speed centrifugation, and virus liberated by three cycles of freeze/thaw. The cell lysate (1 mL in 10 mM Tris, pH 8.1) containing the recombinant virus was amplified and purified. No differences were noted between the growth characteristics of RAPAd5.RSVEGFP and viruses made using standard methods. In the pacAd5 9.2–100 transfected plate, foci were never evident, and virus could not be amplified, confirming an absence of wildtype genome input.

The resultant purified RAPAd5.RSVEGFP particles had a concentration of approximately $8 \times 10^{12}$ particles/mL (1.7 mL total) and an infectious titer of $2 \times 10^{10}$ i.u./mL (infectious units/mL) as determined by HEK293 cell plaque assay (Table I). All assays were performed at least twice.

TABLE 1

Assay for wildtype adenovirus after serial amplification of RAPAd5.RSVEGFP

| Amplification Round | Titer[1] | | Ela copy number |
|---|---|---|---|
| | HEK 293 cells | A549 cells | |
| 2 | $2 \times 10^{10}$ | <1 | 3 |
| 3 | $1 \times 10^{10}$ | <1 | 1 |
| 4 | $5 \times 10^{10}$ | <1 | 4 |
| 10 | $6 \times 10^{10}$ | <1 | 39 |
| 15 | $2 \times 10^{10}$ | <1 | 59 |

[1]Titer is expressed as i.u./mL in HEK 293 cells. A549 cell titer is wildtype titer in $10^9$ particles. The limit of detection is 1 wildtype virion in $10^9$ total particles.
Ela copy number is per $10^9$ adenovirus genomes. The linear range of the assay is from 1 to $10^5$ copies of Ela.

A549 cell overlay and PCR methods were used to determine if any wildtype virus was detectable after the first large-scale amplification and purification. For A549 cell agar overlays, serial dilutions of virus particles were applied to cells at approximately 50% confluence in 3 mL of media (MEM, 4% FBS, 1% Pen/Strep) and 24 hours later overlayed in same plus 0.8% Agar Noble (Difco, Detroit, Mich.). The plates were fed agar-containing media again (2 mL) on day 7 and 13, with the latter also containing neutral red (Sigma, St. Louis, Mo.). Plaques were counted on day 14. No wildtype viral foci were detected for RAPAd5.RSVEGFP generated using the RAPAd.I™ system. The lower limit of sensitivity for the assay is one infectious wildtype virion in $10^9$ virions. This limit is largely due to cell toxicity that occurs when $>10^9$ recombinant particles are used in the primary infection prior to agar overlay.

As an additional test for wildtype virus, A549 cells were infected with recombinant virus at a high particle/cell ratio ($10^5$). After a 2-week incubation all cells on the plate were GFP positive when examined by fluorescence microscopy, but there was no evidence of cytopathic effect. The cells were harvested, pelleted, and lysed by three freeze/thaw cycles. The lysate was used to re-infect a plate of HEK 293 cells. No cytopathic effect was evident after an additional two weeks in culture suggesting that very low to no wildtype virus was present in the initial purified preparation.

In contrast to the A549 plaque overlay, results from virus generated using the RAPAd.I™ system, virus produced by standard co-transfection methods with endonuclease-restricted full-length backbones 5 can contain from $1 \times 10^4$ to $1 \times 10^6$ wildtype plaques per $10^9$ particles. Moreover, E1 a sequences were detected by PCR amplification in 185 out of 292 recombinant lysates. Thus, 63% of recombinant lysates generated using earlier methods required additional rounds of plaque purification. In contrast, standard PCR amplification assays were unable to detect E1a sequences in RAPAd.I™ system-generated virus.

Example 2

Quantitation of Copies of E1a

TaqMan™ PCR (Applied Biosystems, Brachburg, N.J.) was used to quantitate the number of copies of E1a in RAPAd5.RSVEGFP particles. Viral DNA was isolated from purified adenovirus by standard protease treatment and ethanol precipitation methods. Samples (100 ng, 200 nM final concentration, approximately $3 \times 10^9$ adenovirus genomes), primers (900 nM), and probe (200 nM final) were tested for E1a sequences in a Perkin Elmer ABI PRISM 7700 Sequence Detection System. Real-time fluorescence of the probe was monitored. Forward and reverse primer sequences were: 5'-CCA GTG ACG ACG AGG ATG AA-3' (SEQ ID NO:1, bases 951–970 in the adenovirus type 5 genome) and 5'-CCG TAT TCC TCC GGT GAT AAT G-3' (SEQ ID NO:2, bases 1031–1052), respectively. The E1a-specific probe 5'-ACA AGA CCT GCA ACC GTG CCC-3' (SEQ ID NO:3, bases 1010–1030) (MegaBases Evanston, Ill.) contained the fluorescent reporter dye FAM at the 5' end and the quencher TAMRA at the 3' end. A plasmid containing the Ad5 E1a gene was used to generate standard curves, with linearity from $10^0$ to $10^5$ E1a sequences per µl.

Results from TaqMan™ E1a PCR assays showed that the RAPAd5.RSVEGFP particles had 3 E1a genomes per $10^9$ adenovirus genomes (Table 1). In contrast, viruses generated by plaque isolation using standard co-transfection methods[5] with restricted wildtype backbone and shuttle plasmid DNA had approximately 30,000 copies/$10^9$ genomes as detected by TaqMan™ PCR (data not shown).

Example 3

Determination of Wild-type Adenovirus in Recombinant Vector Preparations

Studies have suggested that serial amplification of first generation adenoviruses in HEK293 cells can allow for generation of wildtype adenovirus which can eventually overgrow the recombinant viruses 14. The wildtype virus could arise from recombination of sequences in the recombinant virus backbone with homologous sequences within the 4100 bp left-hand region of the adenovirus genome integrated into HEK293 cells[13]. Alternatively, wildtype virus could be present in low to undetectable levels in the initial isolate; serial amplification would enable amplification of both wildtype and recombinant virus, with the former at a growth advantage. To test if virus made using the RAPAd.I™ system allowed for these possibilities, RAPAd5.RSVEGFP was serially amplified and assayed for wildtype virus at several stages (see Table 1 above).

RAPAd5.RSVEGFP was serially amplified by taking the lysate from one harvest, and using that to re-infect a fresh plate of HEK293 cells. The lysate from this plate was then harvested and subsequently used for the next infection. Virus particles purified from lysates harvested after 2, 3, 4, 10 and 15 rounds of amplification were tested for E1a containing sequences by TaqMan™ PCR titer and replication competent wildtype by A549 plaque assay. The results, listed in Table 1, indicate an absence of infectious wildtype particles as determined by A549 plaque assay, even after 15 serial amplifications. E1a copy number as analyzed by TaqMan™ PCR also remained remarkably low. Together, the data suggest there was no significant increase in wildtype virus upon amplification. There were also no noticeable differences in the growth properties and particle yields between the various preparations.

Example 4

Determination of Reproducibility and Utility of the RAPAd.I™ System

To test the reproducibility and utility of the RAPAd.I™ system, 61 different virus constructs were produced over four months, four to six constructs at a time. Each contained a cDNA sequence encoding a distinct transgene. The virus production was similar to the pilot reporter virus; multiple viral foci were evident and virus-producing cells could be collected after an average of 8 days following transfection into HEK293 cells. All 61 recombinants were found to be functional for the desired protein product. Most important, the quantities of E1a copies per adenovirus genomes ranged from ≦3 to 300 in $10^9$ total viral genomes as tested by TaqMan™ PCR, and A549 wildtype foci assays indicated that the amplified, purified viruses contained <1 wildtype particle in $10^9$ total particles (Table 2).

TABLE 2

Assay for wildtype adenovirus in RAPAd.I ™ virus preparations

| Virus | A549 titer[1] | E1a copy number[2] |
|---|---|---|
| RAPAd5.RSVEGFP | <1 | 3 |
| RAPAd5.CMVsSCLCN3 | <1 | 14 |
| RAPAd5.GLUT4EGFP | <1 | 182/1* |
| RAPAd5.CMVUCP2 | <1 | 33/3* |
| RAPAd5.CMVCGRPIII | <1 | 21/8* |
| RAPAd5.CMVGPXIII | <1 | 300/38* |
| RAPAd5.cav-1-myc | <1 | 71/1* |
| RAPAd5.CMViNOS | <1 | <1 |
| RAPAd5.CMVSODI113T | <1 | <1 |
| RAPAd5.CMVFas | <1 | 2 |
| RAPAd5.RSVmtAeq | <1 | <1 |
| RAPAd5.RSVmMLC | <1 | <1/<1* |
| RAPAd5.PE-hENDO | <1 | <1 |

[1]A549 titer is the number of detectable foci 14 days after inoculation of virus preparations.
[2]E1a copy number is the number of copies of E1a in $10^9$ viral genomes.
*The second number indicates the E1a copy number detected in a second, independent assay.

In summary, an easy, reproducible system for generating recombinant adenovirus has been developed. The novel backbone, when transfected into HEK293 cells along with standard shuttle plasmids containing various transgenes, allowed for the generation of 61 purified, high titer recombinant adenoviruses in four months. Wildtype genomes are not detected by A549 plaque assay and do not overtake recombinant genomes after multiple serial amplifications.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

REFERENCES

1. Shenk, T. Group C adenoviruses as vectors for gene therapy. In: *Viral vectors: gene therapy and neuroscience applications*, edited by Kaplitt, M. G. and Loewy, A. D. San Diego: Academic Press, 1995, p. 43–54.
2. Davidson, B. L. and Roessler, B. J. Adenoviral-mediated gene transfer: potential therapeutic applications. In: *Viral vectors: gene therapy and neuroscience applications*, edited by Kaplitt, M. G. and Loewy, A. D. San Diego: Academic Press, 1995, p. 173–192.
3. Jones N, Shenk T. Isolation of Deletion and Substitution Mutants of Adenovirus Type 5. *Cell* 1978; 13:181–188.
4. Wohlgemuth J G, Kang S H, Nawotka K A, et al. Long-term gene expression from autonomously replicating vectors in mammalian cells. *Gene Ther* 1996; 3(6):503–512.
5. Davidson B L, Doran S E, Shewach D S, et al. Expression of *Escherichia coli* β-galactosidase and rat HPRT in the CNS of *Macaca mulatta* following adenoviral mediated gene transfer. *Exp Neurol* 1994; 125:258–267.
6. Chartier C, Degryse E, Gantzer M, et al. Efficient generation of recombinant adenovirus vectors by homologous recombination in *Escherichia coli. J Virol* 1996; 4805–4810.
7. He T-C, Zhou S, da Costa L T, et al. A simplified system for generating recombinant adenoviruses. *Proc Natl Acad Sci U S A* 1998; 95:2509–2514.
8. Mizucuchi H, Kay M A. Efficient construction of a recombinant adenovirus vector by an improved in vitro ligation method. *Hum Gene Ther* 1998; 9:2577–2583.
9. Souza D W, Armentano D. Novel cloning method for recombinant adenovirus construction in *escherichia coli. Biotechniques* 1999; 26:502–508.
10. Hardy S, Kitamura M, Harris-Stansil T, et al. Construction of adenovirus vectors through Cre-lox recombination. *J Virol* 1997; 71(3):1842–1849.
11. Aoki K, Barker C, Danthinne X, et al. Efficient generation of recombinant adenoviral vectors by Cre-lox recombination in vitro. *Mol Med* 1999; 5(4):224–231.
12. Ng P, Parks R J, Cummings D T, Evelegh c M, et al. A high-efficiency cre/loxP-based system for construction of adenoviral vectors. *Hum Gene Ther* 1999; 10:2667–2672.
13. Graham F L, Smiley J, Russell W C, Naim R. Characteristics of a human cell line transformed by DNA from human adenovirus type 5. *J Gen Virol* 1977; 36:59–74.
14. Lochmuller H, Jani A, Huard J, Prescott S, et al. Emergence of early region 1-containing replication-competent adenovirus in stocks of replication-defective adenovirus recombinants (delta E1+delta E3) during multiple passages in 293 cells. *Hum Gene Ther* 1994; 5:1485–1491.
15. Bett A J, Haddara W, Prevec L, Graham F L. An efficient and flexible system for construction of adenovirus vectors with insertions or deletions in early regions 1 and 3. *Proc Natl Acad Sci USA* 1994; 91:8802–8806.
16. Kojima H, Ohishi N, Yagi K. Generation of recombinant adenovirus vector with infectious adenoviral genome released from cosmid-based vector by simple procedure allowing complex manipulation. *Biochem Biophys Res Commun* 1998; 246:868–872.
17. Ketner G, Spencer F, Tugendreich S, Connelly C, et al. Efficient manipulation of the human adenovirus genome as an infectious yeast artificial chromosome clone. *Proc Natl Acad Sci USA* 1994; 91:6186–6190.
18. Davis A R, Meyers K, Wilson J M. High throughput method for creating and screening recombinant adenoviruses. *Gene Ther* 1998; 5:1148–1152.
19. Crouzet J, Naudin L, Orsini C, Vigne E, et al. Recombinational construction in *Escherichia coli* of infectious adenoviral genomes. *Proc Natl Acad Sci USA* 1997; 94:1414–1419.
20. Fu S, Deisseroth A B. Use of the cosmid adenoviral vector cloning system for the in vitro construction of recombinant adenoviral vectors. *Hum Gene Ther* 1997; 8:1321–1330.
21. Fallaux F J, Bout A, van der Velde I, van den Wollenberg D J, et al. New helper cells and matched early region 1-deleted adenovirus vectors prevent generation of replication-competent adenoviruses. *Hum Gene Ther* 1998; 9(13):1909–1917.
22. Fallaux F J, Kranenburg O, Cramer S J, Houweling A, et al. Characterization of 911: a new helper cell line for the titration and propagation of early region 1-deleted adenoviral vectors. *Hum Gene Ther* 1996; 7(2):215–222.
23. Imler J L, Chartier C, Dreyer D, Dieterle A, et al. Novel complementation cell lines derived from human lung carcinoma A549 cells support the growth of E1-deleted adenovirus vectors. *Gene Ther* 1996; 3(1):75–84.
24. Schiedner G, Morral N, Parks R J, Wu Y, et al. Genomic DNA transfer with a high-capacity adenovirus vector results in improved in vivo gene expression and decreased toxicity. *Nat Genet* 1998; 18:180–183.
25. Samulski R J, Chang L S, Shenk T. Helper free stocks of recombinant adenoassociated viruses: Normal integration does not require viral gene expression. *J Virol* 1989; 63:3822–3828.
26. Bartlett J S, Samulski R J. Genetics and biology of adeno-associated virus. In: Kaplitt M G, Loewy A D.(eds) *Viral vectors: gene therapy and neuroscience applications.* Academic Press: San Diego, 1995, pp 55–73.

What is claimed is:

1. A cloning system for generating recombinant adenovirus, said cloning system comprising:
    (a) an Ad backbone plasmid comprising an Ad genome lacking map units 0 to 9.2, and
    (b) a shuttle plasmid comprising Ad sequences from 0 to 1 and 9.2 to 16.1 map units of an Ad genome,
wherein the numbering of the map units starts with the lefthand ITR.

2. The cloning system of claim 1, wherein an open reading frame constituting E4 in said backbone plasmid comprises a modification.

3. The cloning system of claim 2, wherein the modification is a substitution, insertion, or deletion of one or more nucleotides.

4. The cloning system of claim 1, wherein an open reading frame constituting E3 in said backbone plasmid comprises a modification.

5. The cloning system of claim 4, wherein the modification is a substitution, insertion, or deletion of one or more nucleotides.

6. The cloning system of claim 4, wherein the modification comprises insertion of a multiple cloning site.

7. The cloning system of claim 4, wherein one or more genes required for Herpes Simplex Virus (HSV) packaging and an HSV origin of replication have been placed within the E3 region.

8. The cloning system of claim 1, wherein the backbone plasmid further comprises HSV Amplicon sequences required for packaging and replication.

9. The cloning system of claim 1, wherein the backbone plasmid further comprises one or more sequences that allow for integration of sequences into cells after viral infection.

10. A host cell comprising:
    (a) an Ad backbone plasmid comprising an Ad genome lacking map units 0 to 9.2, and
    (b) a shuttle plasmid comprising Ad sequences from 0 to 1 and 9.2 to 16.1 map units of an Ad genome,
wherein the numbering of the map units starts with the lefthand ITR.

11. The host cell of claim 10, wherein said cell expresses E1 sequences necessary for supporting adenovirus replication.

12. The host cell of claim 11, wherein said cell is an animal cell.

13. The host cell of claim 10, wherein said cell expresses E1, pIX, and E4 sequences required for amplification of viruses generated with an Ad backbone plasmid lacking E1, E4, and/or pIX sequences.

14. The host cell of claim 13, wherein said cell is an animal cell.

15. A method for producing recombinant adenovirus, said method comprising contacting a host cell with:
    (a) an Ad backbone plasmid comprising an Ad genome lacking map units 0 to 9.2, and
    (b) a shuttle plasmid comprising Ad sequences from 0 to 1 and 9.2 to 16.1 map units of an Ad genome,
wherein the numbering of the map units starts with the lefthand ITR.

16. The method of claim 15, further comprising serially amplifying virus produced by said host cell.

17. The method of claim 15, further comprising assaying for the presence of wild type virus.

18. The method of claim 15, wherein said shuttle plasmid further comprises a cDNA of interest.

* * * * *

UNITED STATES PATENT AND TRADEMARK OFFICE
CERTIFICATE OF CORRECTION

PATENT NO.    : 6,830,920 B2
DATED         : December 14, 2004
INVENTOR(S)   : Beverly L. Davidson et al.

It is certified that error appears in the above-identified patent and that said Letters Patent is hereby corrected as shown below:

Title page,
Item [75], Inventors, "Haibin Xia", please delete "US" and insert -- People's Republic of China -- therefor;
Item [56], References Cited, OTHER PUBLICATIONS, second "Fallaux, F.J., et al." reference, after "9" please insert -- (Sept. 1998) --;
"Lochmüller, H., et al." reference, please delete "*t*" and insert -- 5 -- therefor;
"Wohlgemuth, J.G., et al." reference, please delete "trem" and insert -- term -- therefor.

Signed and Sealed this

Thirty-first Day of May, 2005

JON W. DUDAS
*Director of the United States Patent and Trademark Office*